United States Patent
Zahir et al.

(10) Patent No.: US 9,050,325 B2
(45) Date of Patent: Jun. 9, 2015

(54) ONDANSETRON NASAL SPRAY COMPOSITION

(71) Applicants: Abdul Zahir, Lakeville, MA (US); Ryan John Welter, Raynham, MA (US)

(72) Inventors: Abdul Zahir, Lakeville, MA (US); Ryan John Welter, Raynham, MA (US)

( * ) Notice: Subject to any disclaimer, the term of this patent is extended or adjusted under 35 U.S.C. 154(b) by 0 days.

(21) Appl. No.: 13/986,152

(22) Filed: Apr. 8, 2013

(65) Prior Publication Data

US 2014/0303221 A1  Oct. 9, 2014

(51) Int. Cl.
*A61K 31/4164* (2006.01)
*A01N 43/50* (2006.01)
*A61K 31/4178* (2006.01)

(52) U.S. Cl.
CPC ................... *A61K 31/4178* (2013.01)

(58) Field of Classification Search
CPC .................................. A61K 31/4178
USPC ................................................... 514/396, 397
See application file for complete search history.

(56) References Cited

U.S. PATENT DOCUMENTS

| | | | | |
|---|---|---|---|---|
| 5,561,149 A | * | 10/1996 | Azria et al. | 514/397 |
| 5,578,628 A | * | 11/1996 | Tyers et al. | 514/397 |
| 2003/0044356 A1 | * | 3/2003 | Auh et al. | 424/45 |

* cited by examiner

*Primary Examiner* — My-Chau T Tran
(74) *Attorney, Agent, or Firm* — Joseph H. Killion

(57) ABSTRACT

A pharmaceutical composition for treating sudden discomfort associated with nausea and vomiting is disclosed which comprises a therapeutically effective amount of Ondansetron or a pharmaceutical salt thereof formulated for intranaal administration in combination with an antimicrobial preservative yielding enhanced stability of the Ondansetron or pharmaceutical salt thereof with a long chain polymer enhancing the viscosity of the composition.

6 Claims, No Drawings

ONDANSETRON NASAL SPRAY COMPOSITION

BACKGROUND OF INVENTION

Nasal sprays are often preferred over other methods of patient medicament administration such as oral administration, time-release administration or injections where fast patient relief from sudden discomfort associated with nausea and vomiting is the patient's prime consideration.

In situations like those addressed by our invention such as patients suffering from the effects of chemotherapy, migraine headaches, sea sickness, travel (or air) sickness, pregnancy, immediate relief from sudden discomfort associated with nausea and vomiting is necessary and desirable.

Oral introduction of the medicament into the patient's system also takes a significant time to enter the patient's system and bring relief.

Once the time-release medication becomes effective there is administration of medication for a period of time until the medicament is exhausted.

Similarly, administration by injection has drawbacks including the fact that is not usually obtainable quickly enough when needed in the above situations.

An injection brings relief as the medicament spreads into the patient's system until the medicamant is exhausted. An injection does not provide the time-release advantage of medication over a period of time. Another injection may have to be administered later to maintain the therapeutic effect of the medication.

Nasal spray introduction of medicament in an aqueous carrier has the advantage of rapid release into the patient's system to address the needs of those suffering from the above medical situations. However, like injections or oral administration after the medicament is introduced, it produces relief only for a definite period of time until the medicament is expelled from the nasal passages by simply sneezing or vomiting and has to be re-administered.

One of the major hindrances to effective systematic absorption of medications in the nose is due to anatomical features of the epithelium within the nasal cavity. The constant beating off the nasal cilia causes the mucus film to move towards the nasopharynx. This action, in about 8 to 10 minutes, will remove the medicantament from the nasal mucosa reducing the time for effective systematic absorption. The use of thickening, gelling and mucoadhesive agents tends to increase residence on nasal mucosa and therefore increase absorption.

There is a need for a nasal spray of a medicament in an aqueous carrier which rapidly addresses the immediate needs of those suffering from sudden discomfort associated with nausea or vomiting caused by chemotherapy migraine headaches, seasickness, travel sickness, pregnancy and the effects of chemotherapy which provides relief over a more extended period of time than the prior art.

SUMMARY OF INVENTION

We have discovered an improved nasal spray composition and method for the nasal introduction of a medicament into a patient's system for treating a patient suffering from sudden discomfort associated with nausea and vomiting, from the effects of chemotherapy, seasickness, travel (or air) sickness, and pregnancy, which comprises a pharmaceutical composition for treating sudden discomfort associated with nausea and vomiting consisting of a therapeutically effective amount of a medicament or pharmaceutical salt thereof formulated for intranasal administration in combination with a antimicrobial preservative yielding enhanced stability of said medicament or pharmaceutical salt thereof and a long chain polymer enhancing the viscosity of the composition.

We prefer the medicament to be a 5-HT3 receptor antagonist, more particularly a serotonin 5-HT3 receptor antagonist and more particularly Ondansetron ((RS)-9-methyl-3-{(2-methyl-1H-imidazol-1-yl)methyl1}-2,3-dihydro-1H-carbazol-4(9H)-one).

We prefer a therapeutically effective amount of a pharmaceutical salt thereof and more particularly the hydrochloride salt thereof in an aqueous solution and more particularly an aqueous solution consisting of 0.0001-2% by weight/weight of the Ondansetron hydrochloride.

We prefer the long chain polymer to be a cellulose based long chain polymer and more particularly to consist of cellulose polymers and specifically of cellulose polymers having an average molecular weight of 14,000-700,000 and mixtures thereof.

Other viscosity modifiers such as aqueous gels, aqueous emulsions, aqueous suspensions, polyvinyl alcohol and combinations thereof are anticipated but not preferred. I prefer that the long chain cellulose polymers to increase the viscosity of the aqueous solution and promote temporary adhesion to the walls of the nasal passages due to the viscosity of the aqueous solution and the mucoadhesive property of the cellulose polymers binding to nasal mucosa We prefer include the antimicrobial agent and stabilizer to be from 0.01%-2% by weight/weight. There are many stabilizers such as benzalkonium chloride or the equivalents thereof.

Preferably but optionally we include a moisturizing agent more particularly glycerin in our invention to be included 1-7% by weight/volume. Other humectants of the nasal delivery system can be selected from the group including sorbitol, mineral oil, vegetable oil and combinations thereof are anticipated but not preferred Preferably but optionally we include a solubalizing agent in our invention more particularly cyclodextrin from 0.20%-5% by weight/weight. There are many other suitable materials which can be utilized as a solubalizing agent but cyclodextrein is preferred

EXAMPLE 1

Table 1 shows the results of an experiment in which Odansetron was administered by three different methods, including nasal administration.

In vivo Absoprtion

Pharmacokinetic (PK) study was done according to approved protocol including subject informed consent form and Measurement of vital signs under in-house controlled environment of testing by approved professionals. The PK study was three-arms including the administration of each of the following dosage form in a group of 5 patients each.

| Medication | Dosage Form | Strength | Manufacturer |
|---|---|---|---|
| Odansetron | Injection | 4 mg/2 mL | GSK-Australia |
| Odansetron | Tablet | 4 mg | GSK-Australia |
| Odansetron | Nasal Spray | 4 mg/0.2 mL | Test Product |

Each dosage form was administered at time 0 with sampling at 15, 35, 60, 90, 120, 180, and 240 minutes and analysis by qualified HPLC method. The injection was given intramuscularly, tablet was taken orally, whereas, Nasal Spray was administered to nose using conventional pump and actuator by 2 sprays of 100 mcL each. The following results were obtained as percent of the IM injection at various time points.

TABLE 1

| Time (Minutes) | Nasal Spray (% of IM) | Tablet (% of IM) |
|---|---|---|
| 15 | 40 | 0 |
| 35 | 69 | 11 |
| 60 | 47 | 66 |
| 90 | 76 | 105 |
| 120 | 83 | 83 |
| 180 | 57 | 52 |
| 240 | 60 | 104 |

Results:

Nasal Spray gives 69% absorption as compared to injection in the first 35 minutes where oral absorption is only 11%. The concentration from both dosage forms is at almost similar level over the next 4 hours.

Emesis and vomiting are both acute starting within first few hours of chemotherapy as well delayed starting few days later. In travel sickness and pregnancy, the effect is instantaneous. Another type is the anticipatory nausea and vomiting as a result of the expectation of the patient to have nausea and vomiting in these conditions. Nausea and Vomiting effect the quality of life. An effective therapy by the use of a nasal spray with pronounced effect in the first 15 minutes or maybe even earlier as per our invention will improve patient confidence and avoid these conditions.

The long cellulose polymers are utilized as bioadhesives in addition to viscosity enhancers and are used to extend the nasal-cilia clearance time of our nasal spray formulations. Desired properties of a bioadhesive include solubility and compatibility in our nasal spray formulation.

In addition the nasal spray formulation containing the bioadhesive material was evaluated to determine the effect of spray pattern and plume geometry properties The nasal spray composition of our invention was manufactured in a conventional manner by thoroughly mixing the ingredients at ambient temperatures in order to achieve solubility of ingredients and gelling properties Our invention provides numerous advantages over the prior art.

It is an advantage of our invention that it acts quickly to relieve sudden discomfort associated with nausea and vomiting.

It is an advantage of our invention that it remains in the nasal passages for a period of time continuing to provide relief.

Other advantages of our invention are that it is inexpensive to manufacture and easy to prepare. This is a major advantage as the inexpensive ingredients make our invention available to a great number of people who need it and cannot afford more expensive medication. Our aim is to provide a composition that will be readily and widely available to treat a patient suffering from sudden discomfort associated with nausea and vomiting, from the effects of chemotherapy, seasickness, travel (or air) sickness, and pregnancy, Many modifications, changes and adoptions and/or substitutions can be made by those skilled in the art without departing from the scope of our invention. For example a non-aqueous solution or a powder of Ondansetron can be prepared utilizing relevant equivalents of the ingredients in our composition and are anticipated by our invention . The detailed description and example of our invention enhances the understanding of our invention but are not intended to limit the scope of our invention.

Therefore different ingredients or mediums may be substituted by and are anticipated by our invention.

These and other advantages of our invention will become apparent when viewed in light of the accompanying specification.

Accordingly, it is the intention of the inventors to include all such formulations which shall come within the true scope of our invention which is defined by the appended claims.

What we claim is:

1. A pharmaceutical composition for treating sudden discomfort associated with nausea and vomiting, consisting essentially of a therapeutically effective amount of Ondansetron or pharmaceutical salt thereof formulated for intranasal administration in combination with an antimicrobial preservative yielding enhanced stability of said Ondansetron or pharmaceutical salt thereof, and a long chain polymer enhancing the viscosity of the composition wherein the long chain polymer is selected from the group consisting of cellulose polymers having an average molecular weight of 14,000 to 700,000 and mixtures thereof.

2. The pharmaceutical composition of claim 1 further including;
    (a) 1.00% to 7.00% by weight/volume of moisturizing agent.

3. The pharmaceutical composition of claim 2 wherein the moisturizing agent is glycerin.

4. The pharmaceutical composition of claim 1 further including (a)) 0.20% to 5.00% by weight/weight of solubalizing agent.

5. The pharmaceutical composition of claim 4 wherein the solubalizing agent is cyclodextrin.

6. A pharmaceutical composition for treating sudden discomfort associated with nausea and vomiting, consisting essentially of:
    (a) an aqueous nasal spray composition consisting essentially of 0.0001-2% by weight/weight of Ondansetron hydrochloride;
    (b) 1.00% to 7.00% by weight/weight of long chain polymer selected from the group consisting of cellulose polymers having an average molecular weight of about 14,000 to 700,000 and mixtures thereof;
    (c) 1.00% to 7.00% by weight/volume of moisturizing agent;
    (d) 0.01% to 0.2% by weight/weight of antimicrobial preservative and stabilizing agent;
    (e) 0.20% to 5.00% by weight/weight of solubalizing agent.

* * * * *